US012406769B1

(12) United States Patent
Henderson et al.

(10) Patent No.: US 12,406,769 B1
(45) Date of Patent: *Sep. 2, 2025

(54) PATIENT MONITORING SYSTEM

(71) Applicant: Health Care Systems, Inc., Montgomery, AL (US)

(72) Inventors: William Dwight Henderson, Montgomery, AL (US); Reubin Benjamin Felkey, Auburn, AL (US)

(73) Assignee: Health Care Systems, Inc., Montgomery, AL (US)

( * ) Notice: Subject to any disclaimer, the term of this patent is extended or adjusted under 35 U.S.C. 154(b) by 158 days.

This patent is subject to a terminal disclaimer.

(21) Appl. No.: 18/539,631

(22) Filed: Dec. 14, 2023

Related U.S. Application Data

(63) Continuation-in-part of application No. 16/229,691, filed on Dec. 21, 2018, now Pat. No. 11,869,638.

(60) Provisional application No. 62/609,864, filed on Dec. 22, 2017.

(51) Int. Cl.
*G16H 40/67* (2018.01)
*G16H 10/60* (2018.01)

(52) U.S. Cl.
CPC ............. *G16H 40/67* (2018.01); *G16H 10/60* (2018.01)

(58) Field of Classification Search
CPC ......... G16H 10/60; G16H 80/00; G06F 16/22
See application file for complete search history.

(56) References Cited

U.S. PATENT DOCUMENTS

2011/0105854 A1* 5/2011 Kiani ................ G16Z 99/00
600/300

* cited by examiner

*Primary Examiner* — Rachelle L Reichert
(74) *Attorney, Agent, or Firm* — Carmody MacDonald P.C.; Dennis JM Donahue, III; Kevin C. Staed

(57) ABSTRACT

A patient monitoring system helps staff personnel, clinicians and physicians who are making their rounds of patients quickly and accurately enter their reports of patient observations. The patient monitoring system has a monitoring device carried by the staff personnel as they make their rounds which wirelessly communicates with a central server. The monitoring device is populated with patient profile information saved within a centralized server when the monitoring device is in operative communication with the central server and allows the rounding personnel to report their observations back to the server. The monitoring device can also scan a code from a proximity device attached to the patient. The patient information and reported observations are stored by the server in a patient database and are not stored by the monitoring device or by the proximity device which reduces the risk that the patient information will be lost, stolen, or otherwise compromised.

20 Claims, 10 Drawing Sheets

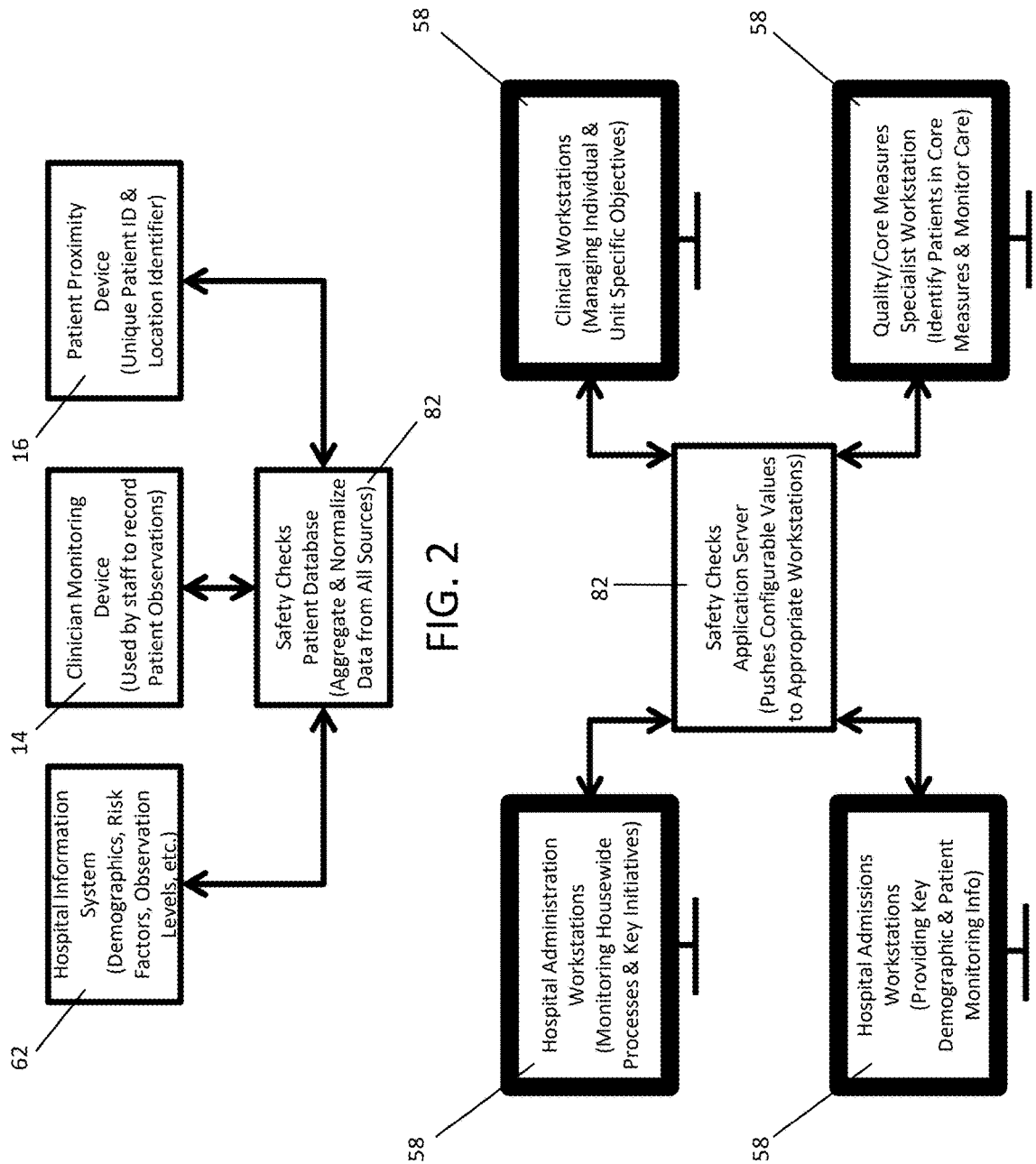

FIG. 4A

| Patient Observation Record | | | | | | | | |
|---|---|---|---|---|---|---|---|---|
| ☑ My Patients  Select My Patients | | | | | | Refresh  ⦿ List  ○ Pictures | Review  Reports | Admin |
| Name | Location | Unit Level | Interval | Risk Factor | Observed Location | Behavior | Behavior Reason | Time |
| TEST, TOM | 339A | Courtyard... | 5 min... | | Bathroom | Appears Sle... | | 19 days |
| TEST, DARLA | 345B | | 15 min... | | Exam Room | Eating | Meeting-Fa... | 15 days |
| TEST, SARA | 339B | Routine | 5 min... | | Courtyard | Talking MD | Court Session | 14 days |
| TEST, JAMIE | 346B | Unit Rest... | 15 min... | Seizure | Bathroom | Crying | Meeting-CM | 14 days |
| TEST, JAMES | 342A | Unit Rest... | 15 min... | | Patient Room | Bathing | Meeting-Phy... | 14 days |
| TEST, SCOTT | 344B | Routine | 15 min... | Seizure | Patient Room | Appears Sle... | | 4 minu... |
| TEST, CHERI | 346A | Courtyard... | 5 min... | Suicide, Elopement, Seizure, ... | Patient Room | Appears Sle... | | 3 minu... |
| TEST, JANE | 341A | Routine | 15 min... | | Patient Room | Appears Sle... | | 2 minu... |
| TEST, BRENDA | 255B | | 15 min... | Elopement | Patient Room | Appears Sle... | | 2 minu... |
| TEST, LEE | 344A | Unit Rest... | 15 min... | Suicide | Patient Room | Appears Sle... | | <2 mi... |
| TEST, JOHN | 341B | Courtyard... | 5 min... | Fall | Patient Room | Appears Sle... | | <2 mi... |
| TEST, FAITH | 345A | Courtyard... | 15 min... | | Patient Room | Appears Sle... | | <2 mi... |

| Unit Level | | Risk Factor | | | | Complete Review |
|---|---|---|---|---|---|---|
| Observed Location | ☐ A/R Dept. | ☐ Bathroom | ☐ Consult Room | ☐ Courtyard | ☐ Dayroom | -Observed Location |
| | ☐ Dining Room | ☐ ECT Suite | ☐ Group-unit | ☐ Gym | ☐ Hall | |
| | ☐ Kitchen | ☐ Meeting Room | ☐ Nurses Station | ☐ Pass-OutofBldg | ☐ Phone | |
| | ☐ Quiet Room | ☐ Rec Room | ☐ Restraint/Secl | ☐ Room | ☐ School | |
| | ☐ Shower | ☐ Transport | ☐ Other <check to edit> | | | -Behavior-may select multiple |
| Behavior | ☐ ADL Noncompliant | ☐ Agitated | ☐ Asleep | ☐ Biting | ☐ Calm | |
| | ☐ Delusional | ☐ Hallucinating | ☐ Hitting | ☐ Hyperactive | ☐ Isolating | -Behavior Reason (context-optional) |
| | ☐ Kicking | ☐ Pacing | ☐ Pinch-Scratch | ☐ Spitting | ☐ Tearful | |
| | ☐ Threatening | ☐ Withdrawn | ☐ Other <check to edit> | | | -Observation Missed Reason |
| Behavior Reason | ☐ Court Session | ☐ Code occurred | ☐ Gym-Removal | ☐ MedPass | ☐ Med Complication | |
| | ☐ Meeting-CM | ☐ Meeting-Family | ☐ Meeting-Physician | ☐ Phone Call | ☐ Phone Call-over | -Notes:Mandatory for missed Observation |
| | ☐ School-Removal | ☐ Visit from Family | ☐ Visit from Other | ☐ Other <check to edit> | | |
| Obs Missed Reason | ○ Unit on Lockdown | ○ Disturbance on the Unit | ○ Other <check to edit> | | | |
| Notes | Double Click to edit multiple lines | | | ☐ Witnessed | | |
| Save | Save and Print | | | Cancel | | |

PATIENT MONITORING SYSTEM

CROSS-REFERENCE TO RELATED APPLICATIONS

This application claims priority from U.S. patent application Ser. No. 16/229,691 filed on Dec. 21, 2018 and U.S. Provisional Patent Application Ser. No. 62/609,864 filed on Dec. 22, 2017, both of which are hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to patient monitoring systems, and more particularly to patient monitoring systems that track whether an observer is within visual range of the patient they are monitoring.

Related Art

Patient monitoring systems have been used within hospital and other institutional settings to assist medical staff in observing and recording inpatient information. In particular, patient monitoring systems are commonly used and developed for psychiatric care facilities to assist caregivers and provide an improved monitoring system than traditional paper files. As explained in US Pat. Pub. No. 2013/0218583 (the '583 Application), staff personnel typically make rounds within a care unit to observe and record the particular activities of each patient within a given care unit. For example, at preset times throughout the course of a night, a staff member required to make rounds through a care unit and record whether a patient is safe, awake or sleeping at a given time. In another example, a staff member may record within the patient file when the patient is given a particular dosage of medicine. As the number of patients within a particular care unit may vary, and the intervals are short, using paper files for recording each event can be cumbersome and ultimately may lead to missed recordings. Accordingly, institutional caregiving facilities have a desire for improved patient monitoring systems that increase efficiency and reduce the probability of human error in the patient monitoring process and provide a mechanism for electronic auditing and validation.

Known monitoring systems, such as that described in the '583 Application have attempted to provide more efficient monitoring systems by saving information related to a particular patient within a preset list and subsequently linking the list to an observation schedule. In operating the system disclosed within the '583 Application, it is suggested that the patient list be uploaded to a transceiver device so that when the transceiver is moved to within an operative distance of a patient outfitted with a transmitting identifier, the transceiver sends an observation time to a central computer which thereby determines whether an observation has been missed depending on when the last observation time was sent. Accordingly, if an observation was missed, an alarm is sent from the central computer to the transceiver. Although such a process may effectively alert staff personnel when an observation has been missed, the system does not effectively provide a substantial improvement to the patient monitoring process where the observer must still manually insert observed activities as the transceiver, central computer and transmitting identifier merely identify the location and most recent observation time.

Like the '583 Application described above, US Pat. Pub. No. 2016/0253470 similarly describes a monitoring system that monitors and tracks staff observations of a patient within a care unit at predetermined time intervals and at predetermined proximities to a patient. In operation, the '470 Application's system functions within the predetermined proximity and time bounds for a particular list of patients and requires additional clarification of observation input when the time period has expired or the staff observer is not within the proximity range This system may effectively track patient location and observation times relative to the observer; however, like the '582 Application, it fails to provide a more efficient means for recording staff personnel observations. Thus, there remains a need in institutional caregiving facilities for an improved monitoring system that not only notifies staff personnel of time intervals between observations and missed observations but also prompts staff personnel for unique observations based on a particular patient.

Another aspect of known monitoring systems is to integrate tablets or portable devices with manual inputs from staff personnel in order to eliminate the necessity of paper files and provide easier access to patient charts. Of course, the patient information collected on these mobile devices is subject to HIPAA regulations and thus there is another desire to those having skill in the art to provide a more secure monitoring system to ensure compliance with HIPAA regulations. In known systems that use mobile devices, patient lists may be uploaded to the mobile device and saved thereon in addition to being sent to a central server. The '583 Application actually suggests that the RFID worn by the patient, such as on a wristband, should store patient information, including name, room number and other relevant information, such as the patient's hospital identification number, diagnosis, risk factors, expected pulse rate and/or other physiological signals to monitor. Accordingly, the '583 Application notes that the signals produced by the wristband which contain the patient information must be in compliance with HIPAA regulations.

In other cases, patient information may be saved on transmitting devices associated with and attached to each patient which subsequently is loaded onto the mobile receiver when a staff member is within a certain range. In these cases, when the information is stored on the mobile device until it is manually downloaded to a remote server or deleted, there is additional expense to the system to ensure that the mobile devices which store patient information comply with HIPAA regulations. It will be recognized that in addition to the expense of the HIPAA compliance for the mobile devices, the storage of patients' personal information away from the central server could still result in the unintended release of the information, such as when a mobile device with the information stored on it has been lost or stolen.

With the issues in the storage and distribution with current healthcare monitoring systems, there has been a desire by institutional healthcare providers to find an improved patient monitoring system that maintains the HIPAA compliance with less cost and preferably increases the reliability and security of the system. Preferably, an improved healthcare monitoring system would offer institutional healthcare providers with a secure way to confirm that staff rounds with patients are performed completely and properly in a timely manner, without missing required observations. The improved system would preferably only store patient information on a central server, not on mobile devices in which the information is being collected by the observer or received from another source nor on a data storage proximity device worn by the patient. Such an improved system would instantaneously save observations to a central server as the mobile device communicates in real-time with the central server and without saving the information on the device. Accordingly, the improved system would increase functionality of the device without unwanted data and would also provide a more secure system in which sensitive patient information is not saved on devices that increase the risk that the information could be compromised.

SUMMARY OF THE INVENTION

The invention described herein is a patient monitoring system that helps staff personnel, clinicians and physicians who are making their rounds of patients quickly and accurately enter their reports of patient observations. The patient monitoring system has a monitoring device carried by the staff personnel as they make their rounds which wirelessly communicates with a central server. The monitoring device is populated with patient profile information saved within a centralized server when the monitoring device is in operative communication with the central server and allows the rounding personnel to report their observations back to the server. The monitoring device can also scan a code from a proximity device attached to the patient. The patient information and reported observations are stored by the server in a patient database and are not stored by the monitoring device or by the proximity device which reduces the risk that the patient information will be lost, stolen, or otherwise compromised.

Another aspect of the invention are the status board interface and the observation entry interface that are shown on the display screen and the notices and alerts associated with these interfaces. Whenever an observer misses a mandatory observation parameter that is provided on the observation entry interface, the computer processor determines that there has been an observation error and causes an alert to be shown on the display screen as a popup window over the observation entry interface so that the observer must select an observation prompt or enter an ad hoc description of the observation. When the patient monitoring system is using the proximity devices, the monitoring device scans the proximity device and relays the proximity device identifier to the server which provides the monitoring device with a positive identification indicator for the patient record associated with the proximity device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings.

FIG. 2 is a schematic diagram of information sources for the patient database.

FIG. 3 is a schematic diagram of the central computer server in communication with computer systems other functional departments in a hospital environment.

FIGS. 4A and 4B illustrate a status board interface on a display screen in patient picture format and in patient list format, respectively.

FIG. 4C illustrates the status board interface on a display screen when connectivity has been lost and reconnection has failed.

FIG. 5 illustrates an observation entry interface on a display screen.

FIGS. 6A-6C illustrate popup windows for the observation entry interface.

FIG. 7 illustrates an observation review interface for a display screen.

DETAILED DESCRIPTION OF THE PREFERRED EMBODIMENTS

Figure 1:
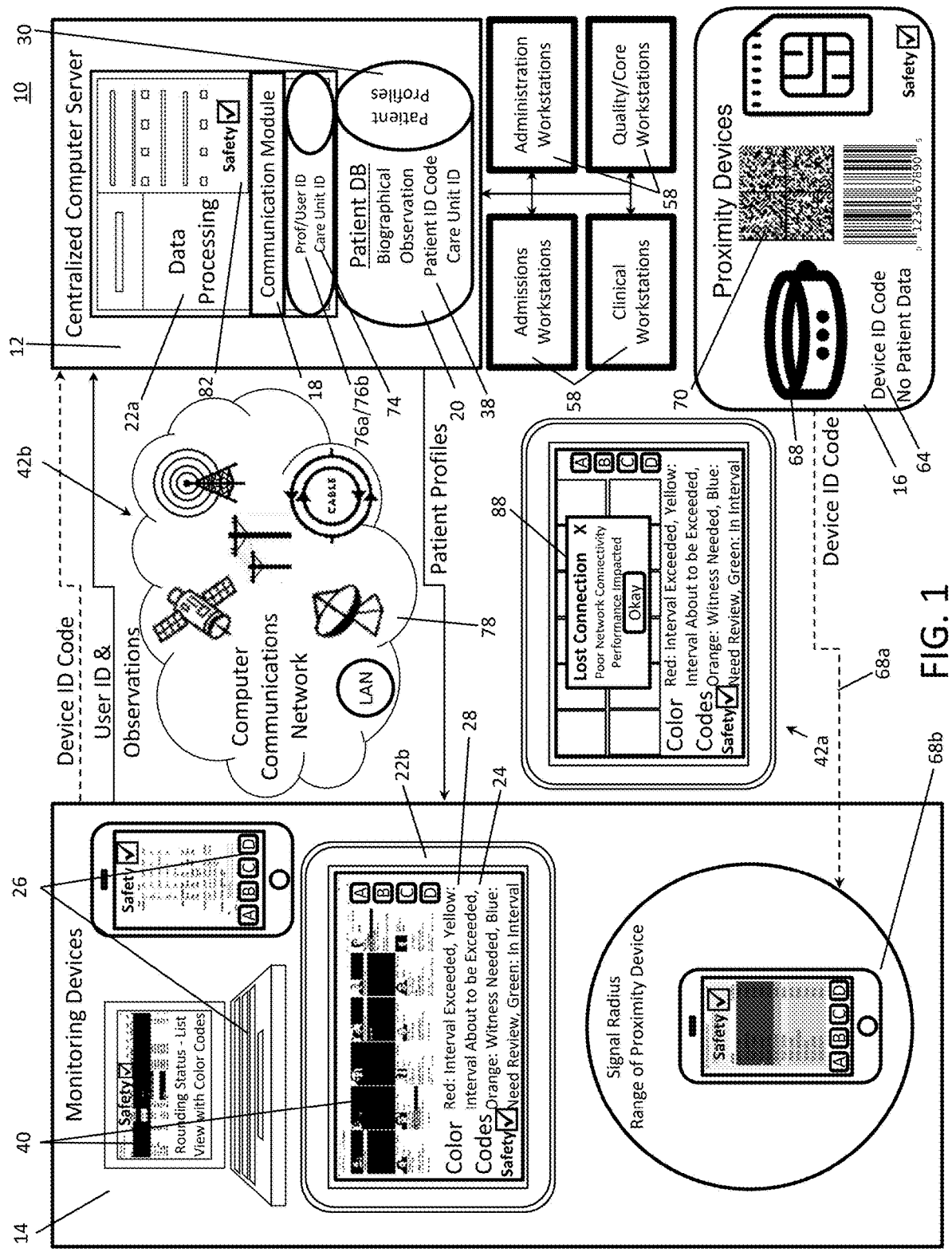
FIG. 1 is a system diagram of a patient monitoring system with monitoring devices that communicate with proximity devices and a central server having a patient database.

The following description of the preferred embodiment(s) is merely exemplary in nature and is in no way intended to limit the invention, its application, or uses.

The invention is a patient monitoring system 10 for aiding staff personnel, clinicians, nurses, and physicians making patient rounds and observations within an institutional setting. As shown in FIG. 1, the Safety Checks patient monitoring system has three primary components which function together: a server 12 that has access to patient information in a patient database, one or more mobile computing devices that are used by the staff personnel who perform rounds, and a set of proximity devices 16 that are worn by or are otherwise physically associated with a corresponding set of patients. Generally, when the computing devices are in wireless communication with the communication module 18 of the server, the server processor 22a will access patient records and other information in the patient database 20 and send the appropriate information to the monitoring devices 14.

As shown in FIG. 2, the patient database preferably aggregates and normalizes data from various sources within the hospital information system so that the information can be stored in the patient database. For example, the patient demographics, risk factors, and observation levels may be retrieved from other databases in the hospital information system 62 to be added into the patient database. The patient observations obtained using the monitoring devices are also added to the patient database as is the information for the patient proximity devices as explained in more detail below. FIGS. 1-3 generally show how the patient monitoring system is preferably a part of and/or integrates with a larger hospital information system that provides secure access to various professionals who operate workstations in the hospital system according to HIPAA regulations. These professionals can include hospital administrators, clinicians and other healthcare providers, admissions staff, quality/core measures specialists, and other functions according to their particular roles and responsibilities.

Figure 4A:
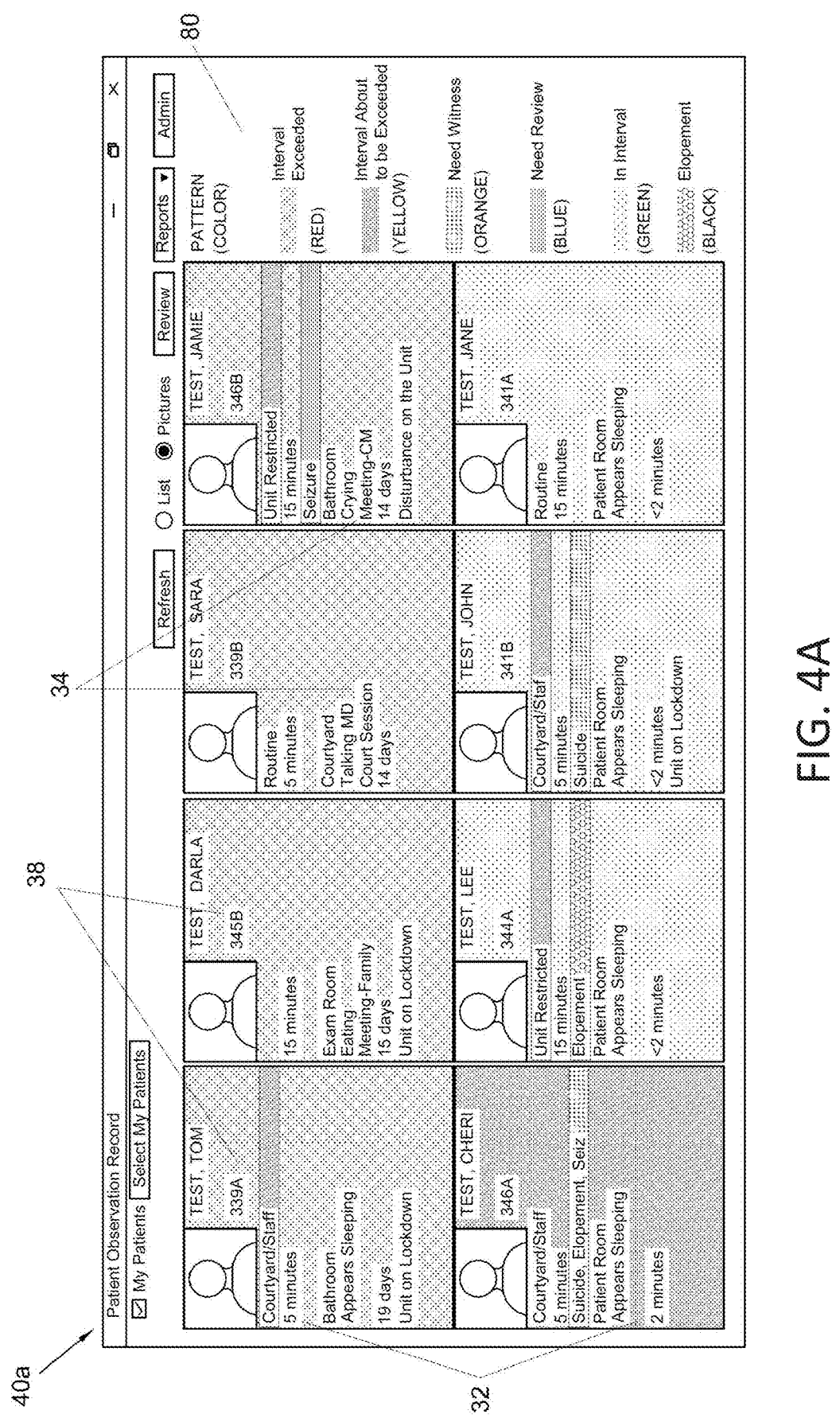

The computing devices have a monitoring software program that runs on their respective processors 22b which control the information being retrieved from the patient database and the observation information being sent back to the server to be stored in the patient database. The software program also causes the computing devices' respective display screens to present a status board interface 40 as shown in FIGS. 4A and 4B and an observation entry interface 46 as shown in FIG. 5. When the computing devices have an active communication link 42b with the server, the patient information received from the patient database can populate the status board interface and the observation information input to the computing device through the observation entry interface can be sent back to the server. The monitoring devices do not store in their data storage modules any patient profiles or other information that they receive from the patient database so if there is no active communication link 42a with the server, there is no data to show on the status board interface and no information will be displayed on the screen. Similarly, without a communication link, since the monitoring devices do not store patient information, there is no patient to particularly identify in the software program for the observation entry interface.

Figure 4C:
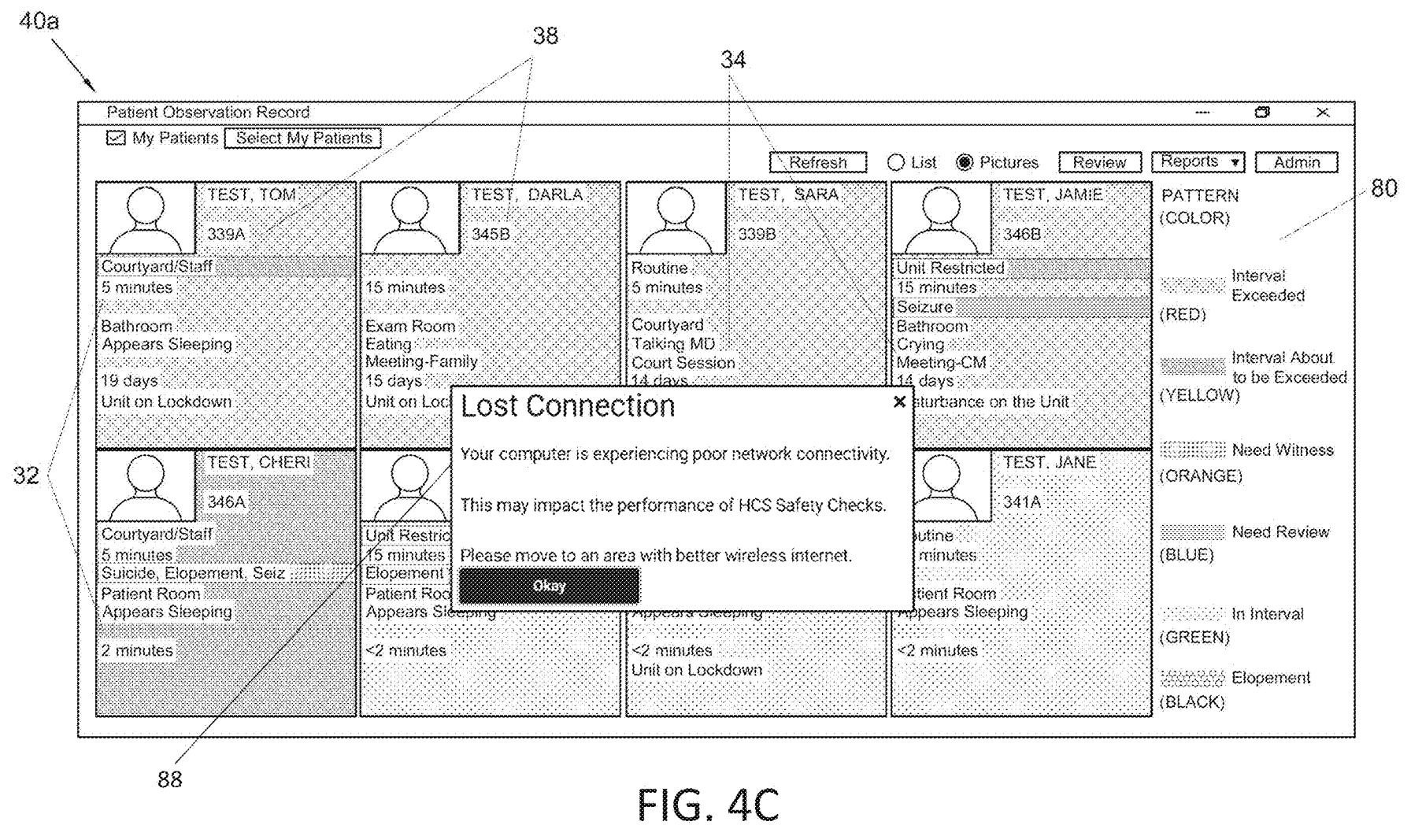

After having had an operative connection between a computing device and the server, if there is a short disruption in wireless communications between the device and the server, typically under thirty (30) seconds, the computing device automatically attempts to reconnect with the server. During such a short disruption, the device's screen continues to display whatever information had been on the screen when the disruption first occurred as a vestige image. If the device is able to reconnect with the server before the user initiates an action requiring the connection with the server, the software performs the same way as if there hadn't been any disruption so no notice is provided to the user. However, if the user initiates an action that requires the connection to the server while the disruption remains, the software will display a banner over the vestige image on the screen notifying the user that the device is attempting to reconnect with the server. Throughout the time period of the disconnection, the user is unable to navigate between different screens or enter any commands or data into the software. If the device fails to reconnect with the server, and the user doesn't initiate any action for an extended period of time, the software will eventually display a banner 88 over the vestige image notifying the user that the connection has been lost, such as shown in FIG. 4C.

The software preferably includes a disconnection timeout feature which will automatically close the screen with the vestige image, and no patient data is stored on the computing device for anyone to see or access once the screen has closed. A baseline disconnection timeout is preferably predefined in the software, such as fifteen (15) minutes, and may be changed by an administrative user who is responsible for the software used by the hospital staff. It will be appreciated that during a period of time with an extended disconnection, users can write their observations on paper as had been done in the past and then enter the information into the patient database with a note explaining that the real-time wireless communications had been unavailable. This data entry can be performed through a workstation terminal with a hardwire connection to the server or using the monitoring device at a later time when wireless service is restored.

According to the present invention, the core software program for the patient monitoring system runs on a centralized computer server that has a server communication module and a server processor as well as the patient database referred to above. The patient database in the monitoring system includes patient profiles 30 for a set of patients 32 that are being monitored. Each one of the patient profiles has patient profile information 34 that includes biographical information 36a and observation information 36b is correlated to a unique patient identification code 38 within the patient database. Additionally, the patient profiles are correlated to patient care unit identifiers 74 in the patient database. Each one of the healthcare professionals who functions within the system has their own unique healthcare professional identifier 76a, and the patient care unit identifiers are correlated to these healthcare professional identifiers. A particular healthcare professional may have roles and responsibilities in several different patient care units, and the healthcare professional identifier for such a professional would be correlated to the patient care unit identifiers that correspond to each one of the units. For example, in the patient database, one set of healthcare professional identifiers can be correlated to one of the patient care unit identifiers while another set of healthcare professional identifiers can be correlated to another patient care unit identifier while yet another set of healthcare professional identifiers can be correlated to both patient care unit identifiers. Additional healthcare professional identifiers can be correlated with other patient care unit identifiers. Generally, the healthcare professionals who have responsibility for the care of patients are defined by the correlations between the patient care identifier and the healthcare professional identifiers.

The mobile monitoring devices are in communication with the server over a wireless communications network to allow the staff personnel to document observations of patients while making their rounds with patients who are located throughout the facility and remotely from the centralized computer server. The monitoring devices are preferably a mobile computing device with a display screen 24, an input device 26, a mobile communication module, a computer processor, and a data storage module 28. Examples of the mobile computing device are a tablet computer, a mobile smartphone, and/or a laptop computer that preferably has a touchscreen serving as the display screen and one of the input devices. As generally indicated above, the computer processor provides the display screen without any patient profile information for any of the patient profiles when there is no connectivity between the server communication module and the mobile communication module. When there is an active communication link, the patient information required for the person making the rounds is received from the server and shown on the status board interface.

The server provides patient information to the mobile monitoring device according to a correlation between the person making the rounds and the patients who are the subject of the observations to be recorded. For example, when gaining access to the core program on the server using the mobile computing devices, the person making the rounds would have entered a unique user identifier 76b to open an active wireless communication link 78 with the centralized computer server, and the server processor would match the user identifier with the person's healthcare professional identifier. The person's user identifier might be identical to their healthcare professional identifier or it may be a correlation of two (2) unique identifiers for the person in the hospital information system. The server processor determines that the healthcare professional identifier is correlated to a patient care unit identifier that is associated with a set of patients in the patient database, and the patient information for these patients is sent back to the mobile monitoring device to populate the status board interface.

It will be appreciated that there can be different interval periods for the rounds of the various patients depending on each one of the individual patients' risk level. For higher risk patients, the observation period would be shorter than lower risk patients. Additionally, the monitoring system can identify patients by their observation status, such as with a color-coding system 80: the patient profile is highlighted red when the time interval between recorded observations has been exceed, yellow when the time interval is about to be exceeded, orange when an observation should be taking place (i.e. witness needed), blue when an observation will be needed shortly, and green when an observation has recently occurred and the status has not yet moved into the observation queue. By identifying patients by their observation status, the monitoring system can allow the person making the rounds to prioritize their observation schedule with patients whose observation interval has been exceeded or is about to be exceeded and then moving to patients that are about to enter or have just entered the window for their observation interval. The observation status is preferably shown with the other patient information on the status board interface, such as with a patient picture format 40*a* as shown in FIG. 4A or a patient list 40*b* format as shown in FIG. 4B.

When the person making the rounds is ready to enter their observations for a patient, they select 44*a* the corresponding patient profile on the status board interface, and the monitoring device opens observation entry interface to input the observation information for the patient. The observation entry interface provides prompts 50 for several observation parameters that the person making the rounds should complete to input the observation information for each patient being monitored. As particularly shown on FIG. 5, observation parameters can include risk factors, observed locations 50*a*, observed behaviors 50*b*, behavior contexts (or reasons for behavior), and reasons for missing an observation 50*c*. Preferably, the observation entry interface shows a list of prompts for each observation parameter with radio boxes that the person making the rounds can select to quickly input the appropriate observation information. The observation entry interface also preferably includes a notes field 84 in which the person making rounds can provide an explanation 86. One of the uses of the notes field is discussed in detail below with reference to the positive identification indicator and proximity devices. The observation information is sent to the server where it is stored with the patient profile in the patient database, and as with the patient information, the observation information is not saved in the monitoring device.

Figure 6A:
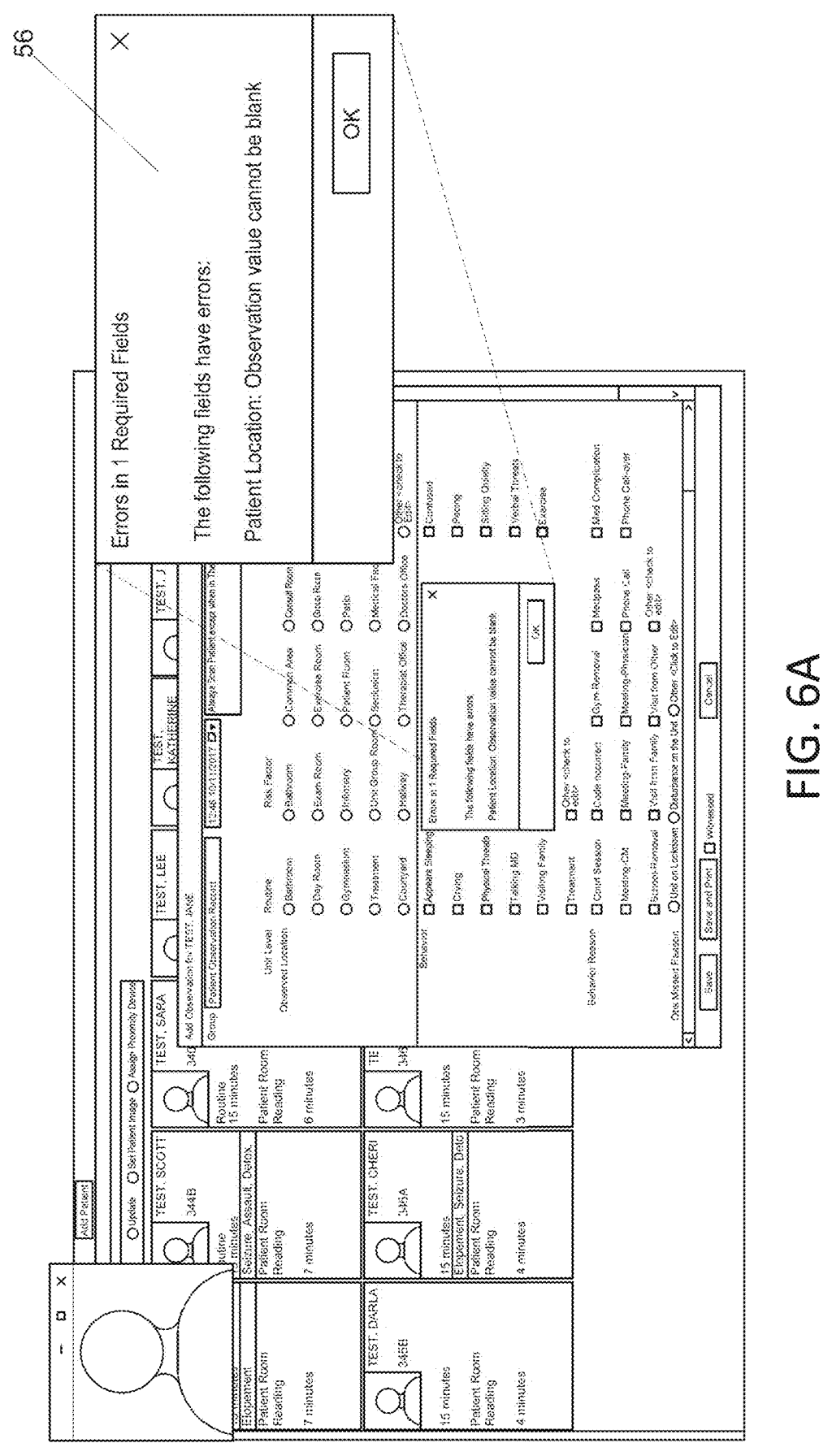

When an observation entry 52 is not entered in response to the prompts for any of the mandatory observation parameters 54 that are provided on the observation entry interface, the computer processor determines that there is an observation error and causes an alert 56 to be shown on the display screen as a popup window over the observation entry interface. An example alert is shown in FIG. 6A. Even when there is no predefined prompt option for a particular observation parameter, each one of the observation parameters has a general "other" prompt that allows the person performing the rounds to input an ad hoc description for the particular observation. Therefore, an entry must be made for each mandatory observation parameter so that no mandatory observation parameter can be accidentally left incomplete.

In one embodiment of the patient monitoring system, proximity devices are physically associated with the patients whose biographical information is stored in the patient database. Preferably, the proximity devices are worn by the patients, such as a bracelet or an anklet, and each proximity device has a unique device identification code 64 that matches the unique patient identification code for the patient wearing the respective proximity device. The device identification code and patient identification code can be matched either by being identical to each other or by being correlated to each other in the patient database. The proximity devices can be active or passive, and regardless of the particular type of proximity device, none of the proximity devices stores any patient profile information. Accordingly, in the case where the device identification code is identical to the patient identification code, the code would not include the patient's social security number, name, birthday, or any other biographical or personally identifiable information for the patient.

The active proximity device 68 has a signal broadcasting module that wirelessly communicates a signal 68*a* within a signal range 68*b*, such as with a Bluetooth® beacon, and in such a case, the signal could include a location identifier along with the device identification code. The mobile communication module of the monitoring device receives the signal with the device identification code when the monitoring device is within the signal range and sends the code to the server. The passive proximity device 70 has a scannable code that only has the device identification code that is entered into the monitoring device through a scan of the proximity device and is then sent to the server. It will be appreciated that the scannable code could be a bar code, matrix code, or other printed code that is scanned through a camera in the mobile computing device or it may be a passive RFID tag that emits a signal only when an RFID reader scans the tag; it is also possible that a scannable code could be a set of characters that can be read by the person performing the rounds and entered into the monitoring device as alphanumeric input.

Whichever type of scanner is used to input the device identification code into the monitoring device, the device identification code is relayed to the centralized computer server by the monitoring device's communication module. The server matches the device identification code with one of the unique patient identification codes for a particular one of the patient profiles stored in the patient database, and the server sends back to the monitoring device a positive identification indicator 66 for the particular one of the patient profiles that is also populated on the status board interface on the display screen. The positive identification indicator can be used to confirm that the person performing the rounds is in the proximity of the patient being observed. There may be times when the person making rounds can observe a patient but cannot get close enough to get the positive identification indicator. In such a case, the person making the rounds knows that they do not have the positive identification indicator for the patient when they enter their observation information into the monitoring device so in addition to selecting the prompts 44*b* for the observation parameters as described above, the person can also add a note explaining the reason that they could not get the positive identification indicator. For example, the person may enter "group therapy session" if the patient is in a group therapy session at the far end of a room that is visible through a window at the other end of the room where the proximity device cannot be scanned, and protocol prohibits interrupting the session.

Figure 6B:
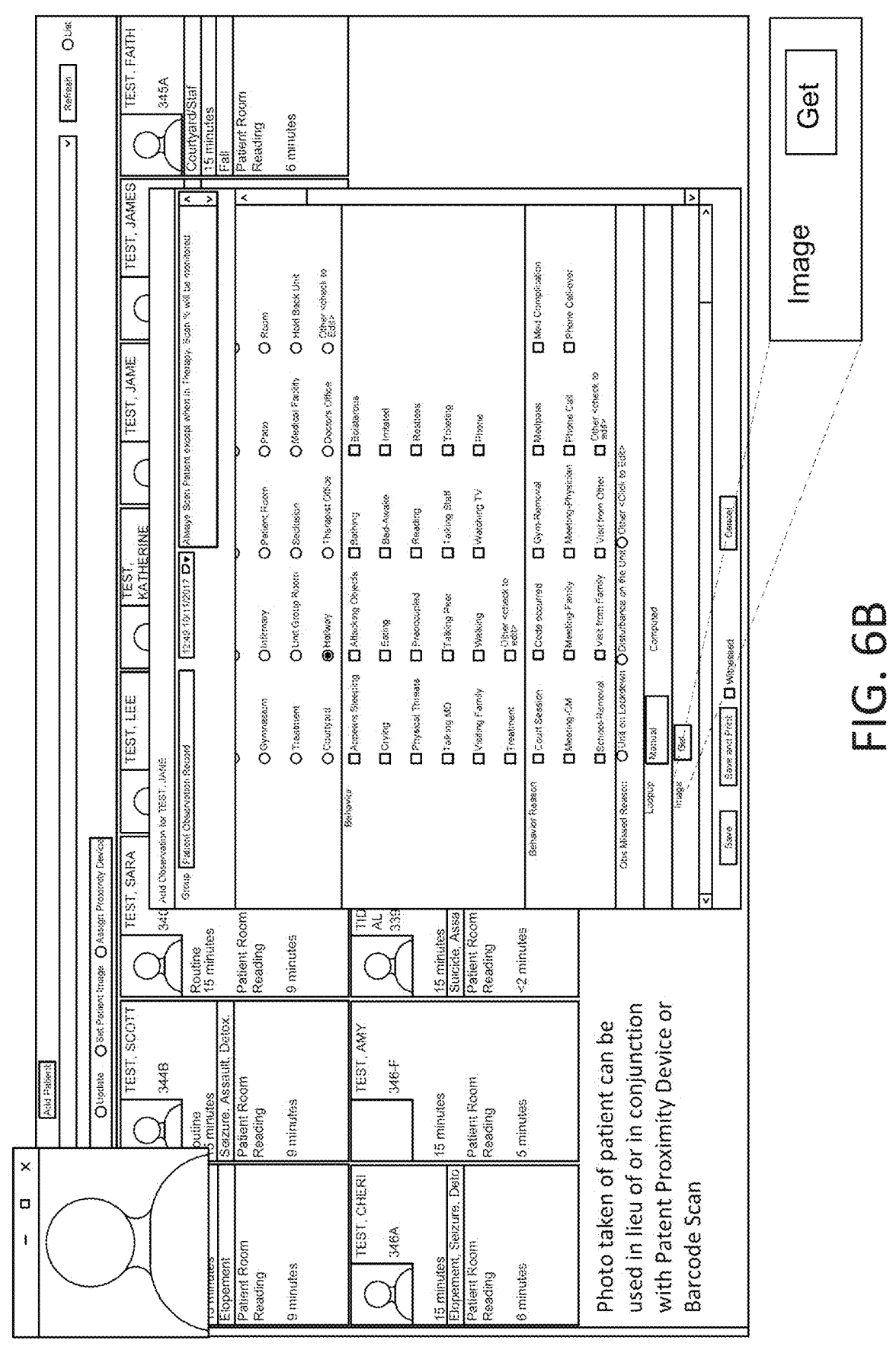
Figure 6C:
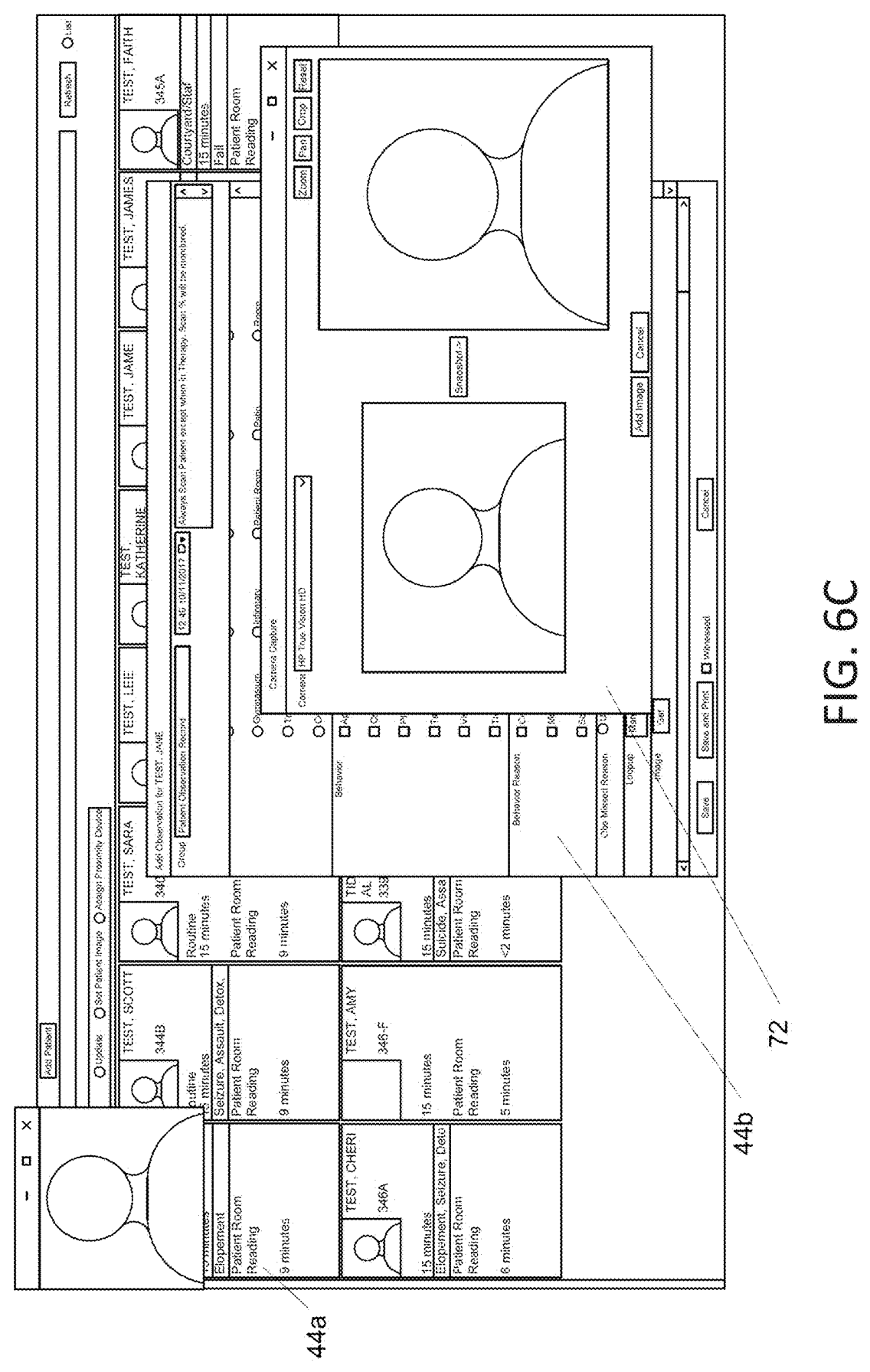

Some hospital systems or other users of the monitoring system may not want the additional expense of proximity devices. In such a case, a real-time photograph of the patient can be used to show that the observer is visually observing the patient rather than the positive identification indicator. It will also be appreciated that photographs, video, and audio could be used apart from or in combination with the positive identification indicator to document exactly what the observer is witnessing. As shown in FIG. 6B, the observer would select the button for some type of recording, and the corresponding input devices 72 in the monitoring device are activated, i.e., the camera and/or microphone. In the recording popup window, shown in FIG. 6C, the observer can select the type of recording (still photo, video, &/or audio), preview what is being recorded and perform some basic controls and editing (zoom, pan, crop, reset), and select the recording to be sent to the server for storage. As with the other observation information, recordings are preferably removed from the memory of the monitoring device when they are sent to the server so that they are not stored on the monitoring device.

Figure 7:
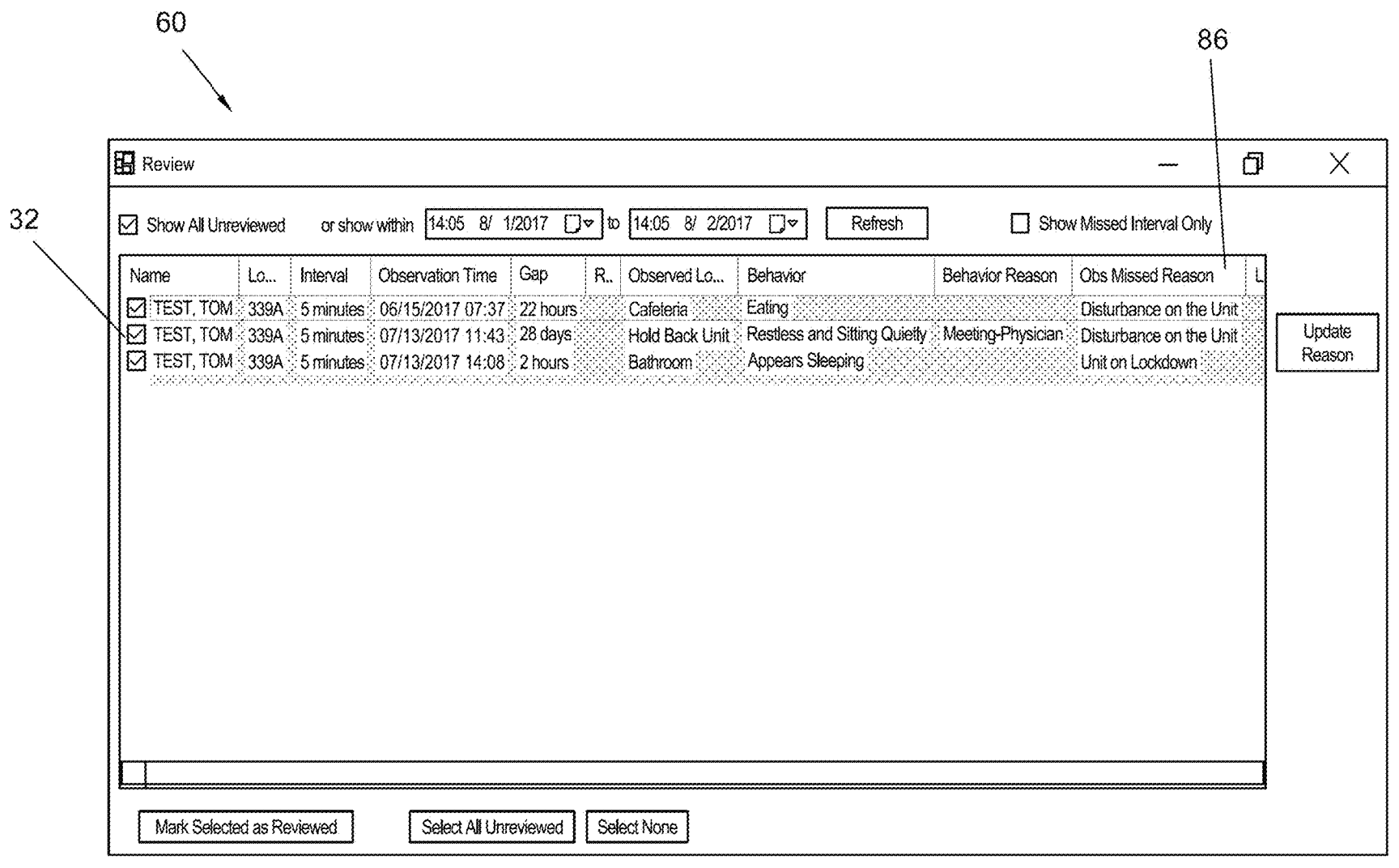

For those patient monitoring systems that use the positive identification indicator with proximity devices, whenever the observer cannot get close enough to the patient being observed to get the positive identification indicator, the observation is flagged for review with a safety report 82. Generally, a nurse periodically performs a "safe patient review" 60 of the patient observations. In some facilities, the review is performed once or twice per shift and in most cases is performed at least once each day or 24-hour period. An example nurse review screen is shown in FIG. 7, and in this particular review, all three (3) patient records being reviewed have a reason provided for the observation being missed ("Disturbance on the Unit" & "Unit on Lockdown"). Additionally, in other instances where there is no positive identification indicator because the patient had to be observed but at a distance, the observer would have entered an explanation in the note field that the nurse can review ("group therapy session" as explained above). The nurse can confirm that the observation status is accurate, check the box for the reviewed observations, and select the button to mark the selected patient records as having been reviewed. The results of the nurse review are also stored in the patient database.

The nurse review may be performed on a mobile computer or on a computer workstation. As shown in FIGS. 1 and 3 and generally indicated above, computer workstations 58 can also be in operative communication with the server within a local area network. The workstations can have different user identifiers for the different functions being performed by the various professionals according to their roles and responsibilities. The user identifiers are entered into the server which matches the user identifiers to healthcare professional identifiers and correlates the professionals to the patient care unit identifier to which they should have access and the amount of access that the particular professional should have to the patient information. For example, the admissions staff may only need to know the particular unit or location where the patient should be placed or is located and may not need to know any of the observation information for the patient, but they may need to be given the unit and location information for every patient in the patient database. In comparison, clinical professionals will have to be given access to the observation information for those patients under their care. Some clinical professionals may only need to access the observation information for those patients in their unit or ward. Other clinical professionals may need to have access to the observation information for every patient in the facility and whose patient profile is in the patient database. The server sends the appropriate level of patient profile information to the workstations for the professionals accordingly.

According to the patient monitoring system described above, the mobile monitoring devices are in communication over a wireless communications network with the server, and the server may be in communication with other computers and devices either wirelessly or through hardwired connections, such as computers and devices used by doctors, nurses, pharmacists, clinicians, and other staff. The mobile monitoring devices are used to report patient observation information to the server where the observation information is stored with the patient's biographical information. The monitoring devices receive patient information from the server that is shown on the display screen while the monitoring devices are in active communication with the server, but the monitoring do not store any of the patient information (observation or biographical), and if connectivity with the server is lost, the monitoring devices will display no information. Additionally, for those implementations of the system that use proximity devices, no patient information is stored on the proximity devices.

In prior art systems, patient profile information might be stored on a personalized proximity device or would be communicated from a server to the monitoring device where it would be stored which has led to the unintended release of personal information, such as when personalized proximity devices or mobile devices have been lost or stolen or when personalized proximity devices are scanned by unauthorized communication devices. The storage of patient information on mobile computing devices or on proximity devices worn by patients compromises the security of the information. According to the present invention, since the proximity device only contains an identification code without any of the patient profile information, and the monitoring device only shows the patients' biographical information and the recorded observations while in communication with the server and without storing any of the patient information, the central server is the only component in the system to store the patient information. Therefore, the architecture of the present patient monitoring system significantly improves the security of the patient information, limits the server to being the only component in the system to be HIPAA compliant which reduces the cost of the system, and reduces the risk that the security of the information will be compromised.

Each patient profile saved within the patient database includes the patient's biographical information, such as name, social security number, birth date, residential address, phone numbers, occupation, employer, insurance provider, emergency contacts, and gender, as well as administrative information, such as room number, treating physician(s), primary care physician, care unit, risk factor(s), and observation interval, observation information for multiple observation parameters. Status parameters may include but are not limited to demographic information, patient risk factors and risk indicators 48a, observed behavioral traits 48c and potential reasons 48d for the observed behavior, date and time indicators, and physical location 48b indicators as well as other general patient observation categories that may be valuable to the observer as they make their observations and record the same, including reasons for missed observations 48e. In the preferred embodiment, a complete observation report includes a selection of patient's location at the time of observation and the observed behavior of the patient, and it may also include the context for the behavior or the perceived rationale for the patient's behavior. In the case where an observation is missed, the system requires that the observer include a reason for why the observation was missed before they are permitted to continue the session.

The safety check and reporting system 82 of the present invention uses secure components to ensure compliance with HIPAA regulations. For example, the system uses industry standard encryption methods for data as it is being stored and displayed and when the data is being communicated. Additionally, as explained above, the patient proximity device does not store patient data, preventing it from being compromised and avoiding it becoming an access point from which patient information might be stolen or through which unauthorized access to the patient data may be obtained. The clinician monitoring device uses a software-as-a-service (SAAS) connection to the database and has no patient data stored on it locally which reduces its risk of being compromised and avoiding it becoming an access point from which patient information might be stolen or through which unauthorized access to the patient data may be obtained.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, the server's communications module can include a wireless router that provides for Wi-Fi communication with the monitoring devices and can also communicate with workstation computer terminals through a local area network over hardwired connections; additionally, the communications module can allow for cellular phone communications over a distributed communications network such as the internet. The various protocols for wireless and hardwired communications are well known to persons of ordinary skill in the art, and future communication protocols can be implemented with the monitoring system described above without departing from the invention. Thus, the breadth and scope of the present invention should not be limited by any of the above-described exemplary embodiments, but should be defined only in accordance with the following claims appended hereto and their equivalents.

What is claimed is:

1. A patient monitoring system, comprising:
 a centralized computer server, wherein the centralized computer server is comprised of a server communication module, a patient database, and a server processor, wherein the patient database is comprised of a full set of patient profiles for a corresponding set of patients being monitored, and wherein each of the patient profiles within the full set of patient profiles is comprised of patient profile information;
 a monitoring device located remotely from the centralized computer server, wherein the monitoring device comprises a display screen, an input device, a mobile communication module, a computer processor, and a data storage module, wherein the computer processor populates a status board interface on the display screen with patient profile information for at least a partial set of patient profiles received from the patient database when the monitoring device is in operative communication with the centralized computer server at a first time, wherein the computer processor populates the status board interface on the display screen with patient profile information without saving the patient profile information in the data storage module, wherein the input device receives a first selection of one of the patient profiles shown on the status board interface, wherein the monitoring device loses communication with the centralized computer server at a second time following the first time and there is no communication link between the server communication module and the mobile communication module for a disconnection time period following the second time, and wherein the computer processor and the display screen have none of the patient profile information for any of the patient profiles during the disconnection time period following the second time; and
 a plurality of computer workstations in operative communication with the centralized computer server within a local area network.

2. The patient monitoring system of claim 1, wherein the computer processor provides a notice on the display screen during at least a portion of the disconnection time period indicating that there is no communication link.

3. The patient monitoring system of claim 1, wherein the mobile communication module automatically attempts to reconnect the communication link with the centralized computer server during the disconnection time period.

4. The patient monitoring system of claim 1, wherein the computer processor has a disconnection timeout at an end of the disconnection time period, and wherein the computer processor closes the display screen when there is no communication link at the end of the disconnection time period.

5. The patient monitoring system of claim 1, wherein a first set of workstations provides a first set of user identifiers to the centralized computer server, wherein a second set of workstations provides a second set of user identifiers to the centralized computer server, wherein a third set of workstations provides a third set of user identifiers to the centralized computer server, wherein the server processor matches the first set of user identifiers to the first set of healthcare professional identifiers and correlates the first set of user identifiers to the first patient care unit identifier, wherein the server processor matches the second set of user identifiers to the second set of healthcare professional identifiers and correlates the second set of user identifiers to the second patient care unit identifier, wherein the server processor matches the third set of user identifiers to the third set of healthcare professional identifiers and correlates the third set of user identifiers to both the first patient care unit identifier and the second patient care unit identifier, wherein the centralized computer server sends to the first set of workstations a first set of patient profile information correlated to the first patient care unit identifier, wherein the centralized computer server sends to the second set of workstations a second set of patient profile information correlated to the second patient care unit identifier, and wherein the centralized computer server sends to the third set of workstations both the first set of patient profile information and the second set of patient profile information.

6. The patient monitoring system of claim 1, wherein each one of the patient profiles in the partial set of patient profiles is correlated to a patient care unit identifier in the patient database, wherein a set of healthcare professional identifiers is correlated to the patient care unit identifier in the patient database, wherein the monitoring device opens an active wireless communication link with the centralized computer server and provides a user identifier to the centralized computer server, wherein the server processor matches the user identifier with a healthcare professional identifier correlated to the patient care unit identifier, wherein the server processor retrieves from the patient database the patient profile information for the partial set of patient profiles with the patient care unit identifier, and wherein the server communication module sends the patient profile information for the partial set of patient profiles to the monitoring device only when the monitoring device is in operative communication with the centralized computer server through the active wireless communication link.

7. The patient monitoring system of claim 1, wherein the patient profile information is comprised of biographical information and observation information, wherein the patient profile information for each one of the patient profiles is correlated to a unique patient identification code within the patient database, and wherein the computer processor provides the display screen with an observation entry interface in response to the first selection while there is the operative communication.

8. The patient monitoring system of claim 7, further comprising a plurality of proximity devices physically associated with the set of patients whose biographical information is stored in the patient database.

9. The patient monitoring system of claim 8, wherein each one of the proximity devices is further comprised of a unique device identification code matching the unique patient identification code for each corresponding one of the patient profiles for the set of patients.

10. The patient monitoring system of claim 9, wherein none of the proximity devices stores any patient profile information, wherein an entry of the unique device identification code into the monitoring device through at least one of the input device and the mobile communication module is relayed to the centralized computer server, wherein the server processor matches the unique device identification code received from monitoring device with the unique patient identification code for a particular one of the patient profiles stored in the patient database, and wherein the centralized computer server provides to the monitoring device a positive identification indicator for the particular one of the patient profiles that is populated on the status board interface on the display screen.

11. A patient monitoring system, comprising:
  a centralized computer server, wherein the centralized computer server is comprised of a server communication module, a patient database, and a server processor, wherein the patient database is comprised of a full set of patient profiles for a corresponding set of patients being monitored, wherein each of the patient profiles within the full set of patient profiles is comprised of patient profile information, wherein the patient profile information is comprised of biographical information and observation information, and wherein the patient profile information for each one of the patient profiles is correlated to a unique patient identification code within the patient database;
  a monitoring device located remotely from the centralized computer server, wherein the monitoring device comprises a display screen, an input device, a mobile communication module, a computer processor, and a data storage module, wherein the computer processor populates a status board interface on the display screen with patient profile information for at least a partial set of patient profiles received from the patient database when the monitoring device is in operative communication with the centralized computer server at a first time, wherein the computer processor populates the status board interface on the display screen with patient profile information without saving the patient profile information in the data storage module, wherein the input device receives a first selection of one of the patient profiles shown on the status board interface, wherein the computer processor provides the display screen with an observation entry interface in response to the first selection while there is the operative communication, wherein the monitoring device loses communication with the centralized computer server at a second time following the first time and there is no communication link between the server communication module and the mobile communication module for a disconnection time period following the second time, and wherein the computer processor and the display screen have none of the patient profile information for any of the patient profiles during the disconnection time period following the second time; and
  a plurality of computer workstations in operative communication with the centralized computer server within a local area network.

12. The patient monitoring system of claim 11, further comprising a plurality of proximity devices physically associated with the set of patients whose biographical information is stored in the patient database.

13. The patient monitoring system of claim 11, wherein the computer processor provides a notice on the display screen during at least a portion of the disconnection time period indicating that there is no communication link.

14. The patient monitoring system of claim 11, wherein the mobile communication module automatically attempts to reconnect the communication link with the centralized computer server during the disconnection time period.

15. The patient monitoring system of claim 11, wherein the computer processor has a disconnection timeout at an end of the disconnection time period, and wherein the computer processor closes the display screen when there is no communication link at the end of the disconnection time period.

16. A patient monitoring system, comprising:
  a centralized computer server, wherein the centralized computer server is comprised of a server communication module, a patient database, and a server processor, wherein the patient database is comprised of a full set of patient profiles for a corresponding set of patients being monitored, wherein each of the patient profiles within the full set of patient profiles is comprised of patient profile information, wherein the patient profile information is comprised of biographical information and observation information, wherein the patient profile information for each one of the patient profiles is correlated to a unique identification code within the patient database and to at least one of a first patient care unit identifier and a second patient care unit identifier in the patient database, wherein a first set of healthcare professional identifiers is correlated to the first patient care unit identifier in the patient database, wherein a second set of healthcare professional identifiers is correlated to the second patient care unit identifier in the patient database, and wherein a third set of healthcare professional identifiers is correlated to both the first patient care unit identifier and the second patient care unit identifier in the patient database;
  a plurality of computer workstations in operative communication with the centralized computer server within a local area network, wherein a first set of workstations provides a first set of user identifiers to the centralized computer server, wherein a second set of workstations provides a second set of user identifiers to the centralized computer server, wherein a third set of workstations provides a third set of user identifiers to the centralized computer server, wherein the server processor matches the first set of user identifiers to the first set of healthcare professional identifiers and correlates the first set of user identifiers to the first patient care unit identifier, wherein the server processor matches the second set of user identifiers to the second set of healthcare professional identifiers and correlates the second set of user identifiers to the second patient care unit identifier, wherein the server processor matches the third set of user identifiers to the third set of healthcare professional identifiers and correlates the third set of user identifiers to both the first patient care unit identifier and the second patient care unit identifier, wherein the centralized computer server sends to the first set of workstations a first set of patient profile information correlated to the first patient care unit identifier, wherein the centralized computer server sends to the second set of workstations a second set of patient profile information correlated to the second patient care unit identifier, and wherein the centralized computer server sends to the third set of workstations both the first set of patient profile information and the second set of patient profile information; and a monitoring device located remotely from the centralized computer server, wherein the monitoring device comprises a display screen, an input device, a mobile communication module, a computer processor, and a data storage module, wherein the monitoring device opens an active wireless communication link with the centralized computer server at a first time and provides a unique user identifier to the centralized computer server, wherein the server processor matches the unique user identifier with a unique healthcare professional identifier in the first set of healthcare professional identifiers, wherein the centralized computer server sends to the monitoring device the first set of patient profile information correlated to the first patient care unit identifier only when the monitoring device is in operative communication with the centralized computer server through the active communication link, wherein the computer processor populates the status board interface on the display screen with the patient profile information for the first set of patient profiles stored in the patient database when the monitoring device is in operative communication with the centralized computer server, wherein the monitoring device loses communication with the centralized computer server at a second time following the first time and there is no communication link between the server communication module and the mobile communication module for a disconnection time period following the second time, and wherein the computer processor and the display screen have none of the patient profile information for any of the patient profiles during the disconnection time period following the second time.

17. The patient monitoring system of claim 16, wherein the input device receives a first selection of one of the patient profiles shown on the status board interface, and wherein the computer processor provides the display screen with an observation entry interface in response to the first selection.

18. The patient monitoring system of claim 17, wherein the computer processor populates the status board interface on the display screen with patient profile information without saving the patient profile information in the data storage module, wherein the observation information is further comprised of a set of observation parameters selected from the group of parameters consisting of a set of risk factors, a set of observed locations, a set of observed behaviors, a set of behavior contexts, a set of reasons for missing an observation, and any combination thereof.

19. The patient monitoring system of claim 16, wherein the computer processor provides a notice on the display screen during at least a portion of the disconnection time period indicating that there is no communication link.

20. The patient monitoring system of claim 16, further comprising a plurality of proximity devices physically associated with the set of patients whose biographical information is stored in the patient database, wherein each one of the proximity devices is further comprised of a unique device identification code matching a unique patient identification code for each corresponding one of the patient profiles for the set of patients, wherein none of the proximity devices stores any patient profile information, wherein an entry of the unique device identification code into the monitoring device through at least one of the input device and the mobile communication module is relayed to the centralized computer server, wherein the server processor matches the unique device identification code received from monitoring device with the unique patient identification code for a particular one of the patient profiles stored in the patient database, and wherein the centralized computer server provides to the monitoring device a positive identification indicator for the particular one of the patient profiles that is populated on the status board interface on the display screen.

* * * * *